Figure 1:
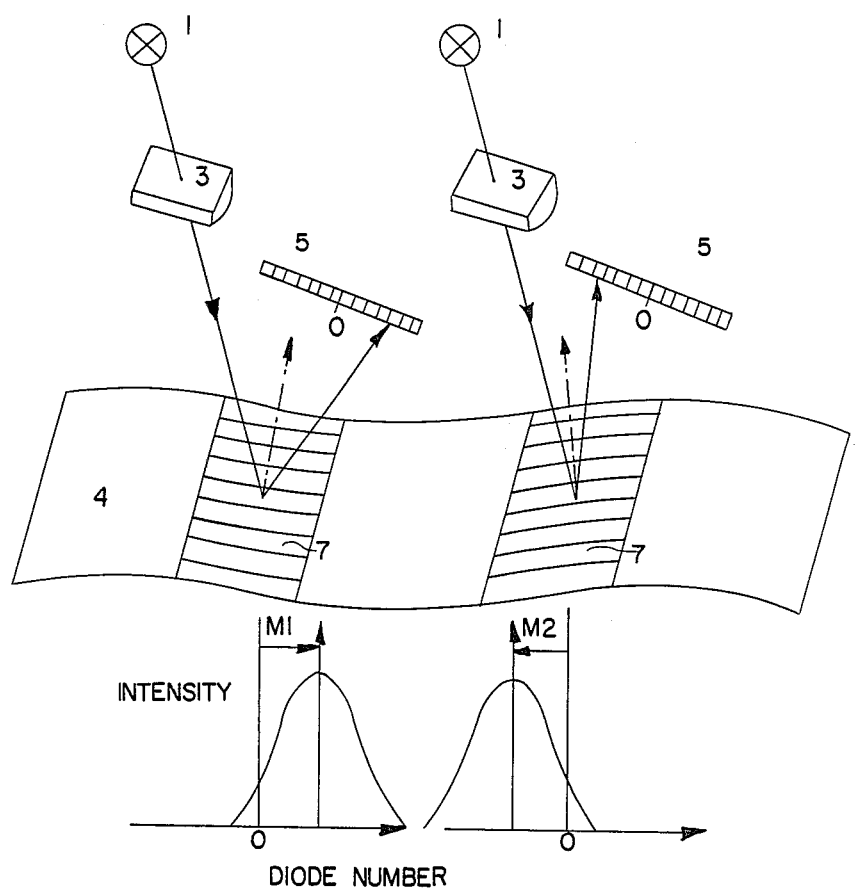

United States Patent [19]

Rau et al.

[11] Patent Number: 4,763,006
[45] Date of Patent: Aug. 9, 1988

[54] DEVICE DETERMINING SURFACE ELEMENT INCLINATION ANGLE FOR THE OPTICAL DETECTION OF FORM ERRORS OF A LOW ORDER

[75] Inventors: Norbert Rau, Kirchheim/Teck; Gerd Hübner, Stuttgart; Wolfgang Staiger, Möglingen; Rainer Brodmann, Haar; Oskar Gerstorfer, Dachau, all of Fed. Rep. of Germany

[73] Assignee: Optische Werke G. Rodenstock, Munich, Fed. Rep. of Germany

[21] Appl. No.: 925,802

[22] PCT Filed: Feb. 5, 1986

[86] PCT No.: PCT/DE86/00037

§ 371 Date: Dec. 3, 1986

§ 102(e) Date: Dec. 3, 1986

[87] PCT Pub. No.: WO86/04676

PCT Pub. Date: Aug. 14, 1986

[30] Foreign Application Priority Data

Feb. 5, 1985 [DE] Fed. Rep. of Germany ....... 3503858

[51] Int. Cl.$^4$ ............... G01N 21/86; G01B 11/30; G01B 11/24
[52] U.S. Cl. .................. 250/561; 356/371; 356/376
[58] Field of Search ............. 250/561, 562, 559, 563, 250/571, 572; 356/376, 1, 4, 371, 377, 429, 430, 375

[56] References Cited

U.S. PATENT DOCUMENTS

| | | | |
|---|---|---|---|
| 3,857,637 | 12/1974 | Obenreder | 356/371 |
| 3,866,038 | 2/1975 | Korth | 356/375 |
| 4,332,477 | 6/1982 | Sato | 356/371 |
| 4,377,341 | 3/1983 | Task et al. | 356/371 |
| 4,390,277 | 6/1983 | Quinn | 356/371 |
| 4,411,528 | 10/1983 | Newcomb et al. | 356/120 |
| 4,412,743 | 11/1983 | Eberly | 356/371 |
| 4,449,818 | 5/1984 | Yamaguchi et al. | 356/371 |
| 4,534,650 | 8/1985 | Clerget et al. | 356/376 |
| 4,660,970 | 4/1987 | Ferrano | 356/376 |

FOREIGN PATENT DOCUMENTS 0110146 10/1983 European Pat. Off. .
57-49805 3/1982 Japan .

OTHER PUBLICATIONS

Brodmann et al., "Optical Roughness Measuring Instrument for Fine-Machined Surfaces," *Optical Engineering* vol. 24, No. 3, 6/85, pp. 408–419.
Bertani et al. "A Fast Optical Profilometer", *Optical Communications* vol. 46, No. 1, 6/83, pp. 1–3.

*Primary Examiner*—David C. Nelms
*Assistant Examiner*—Michael Messinger
*Attorney, Agent, or Firm*—& Gilster Kalish

[57] ABSTRACT

A device is provided for the optical detection of form errors of a low order, for example of roughness. The device possesses a light source whose light probes the body to be examined and a light-receiving device for the light reflected by the body. The device is characterized by the fact that the light-receiving device consists of a number of light-receiving elements arranged in linear array and that an evaluation unit determines the inclination angle of the probed surface element of the body from all output signals of the light-receiving elements. Shifts in the core of the reflected light beam can be measured which are substantially below the width of a light-receiving element. The measuring results remain practically unaffected by form deviations of a higher order such as roughness etc.

11 Claims, 5 Drawing Sheets

DEVICE DETERMINING SURFACE ELEMENT INCLINATION ANGLE FOR THE OPTICAL DETECTION OF FORM ERRORS OF A LOW ORDER

DESCRIPTION

1. Technical Background

The invention relates to a device for the detection of form deviations of a low order and, in particular, of form deviations of the first or second order.

Form deviations of the first to third orders are described as roughness, waves or grooves. (Form deviations of the second order are sometimes also described as "chatter marks). This type of form deviations and, in particular, form deviations of the second order result, for example, in the low frequency range in noise development such as whistling in bearing surfaces of transmission shafts. The occurrence of whistling necessitates the disassembly of the transmission to remove the shaft. To avoid this time-consuming effort, it would be desirable, for example during the assembly of the transmission, to check all shafts for the occurrence of form deviations and/or form errors of a low order and, in particular, for the occurrence of chatter marks which cause noise, prior to assembly.

2. State of the Art

Up until now, form deviations of a low order have been measured industrially only with mechanical form testing instruments such as, for example, the "Perthen-Formtester" of Messrs. Mahr. However, a mechanical form testing does not only have the disadvantage that it requires a relatively great deal of time but also that it requires a great deal of effort to perform the form testing: For example, the test stand must be free of low-frequency building vibrations.

It has nevertheless been found that even when a great deal of effort is invested in the instruments, the results of mechanical form testing cannot always be used as a reliable assessment of whether, for example, a transmission shaft will "whistle" once installed. For this reason, it has already been suggested that form deviations of a lower order be assessed optically (Annals of the CIRP Vol. 33/1/1984, Page 407 f.). With this known device for an optical detection of surface defects, the angle of reflection or the change in this angle of reflection of the reflected beam which results from form deviations is measured using "light scales" consisting of two photodiodes.

However, this known device has several disadvantages: A measurement using light scales consisting of two photoreceivers does not permit a free choice in the spot size of the examining light beam on the surface to be examined for a certain, desired angular resolution. In addition, a relatively large electronic and optical effort is required for a control of the intensity of the examining light beam.

Above all, however, form deviations of a higher order, for example, the roughness of the surface, have a comparatively great influence on the measuring results due to the "splitting up" of the light beam caused by the roughness.

Representation of the Invention

The object of this invention is to present a device for the optical detection of form deviations and/or surface errors of a low order with which form deviations of a low order can be assessed with high precision with a comparatively low optical and electronic effort.

This object is solved according to the invention by having a device such as is known from "Annals of the +IRP, Vol. 33/1/1984, Page 407 f.", as a base device and then further developing this device with the features of the characterising part.

In accordance with this invention it has been recognised that a high-precision angular resolution is possible when the light-receiving device consists of a number of light-receiving elements arranged in a line and when the output signals of all light-receiving elements are evaluated in the determination of the angle of inclination. In this way, it is surprisingly possible to resolve shifts in the core of the reflected light beam which are considerably below the width of a light-receiving element. The process in accordance with the invention also has the further surprising advantage that the measuring results obtained remain practically uninfluenced by form deviations of a higher order such as roughness, etc. Nevertheless, the device in accordance with this invention makes it possible to determine several measuring values simultaneously, such as the statistical local roughness, the roughness integrated over the measuring spot, the waveness, form and locality deviation in the integrated profile as well as the sight test or the chatter marks in the slope profile.

In addition, by changing the size of the measuring spot, a certain filter effect can be obtained with which the influence of the roughness on the measuring signal can be separated from the influence of the waviness.

A further advantage of the device according to this invention is that the optical testing head is less sensitive than a mechanical probe to irritant vibrations sent out by the object being tested. This applies both to vibration directions in the plane of the object's to be tested surface as well as perpendicular to this. This allows the possibility of integrating the device according to this invention in a production line. The device according to this invention is also largely insensitive to distance changes within a comparatively large range.

Further refinements of the development are given in the sub-claims.

An equation is given below according to which the evaluation unit determines the inclination angle of the probed surface element from the output signals of the individual light-receiving elements. This equation permits, without any great effort, the assessment of shifts in the core of the reflected light beam on the array of light-receiving elements which can be less than 10% of the width of a light-receiving element. The equation used in accordance with this invention also permits the automatic positioning of the device to an actual surface in such a way that the optical axis lies in the surface normal. As a result and in contrast to mechanical probes, it is not necessary to perform multiple probes.

Said equation is as follows:

$$\alpha \cong \tfrac{1}{2}\tan(2\alpha) = \frac{b}{2n_{ges}f} \sum_{j=-(k-1)}^{l} n_j x_j$$

where $$n_{ges} = \sum_{j=-(k-1)}^{l} n_j$$

$k + 1$:     number of light-receiving elements
$n_j$:     amplitude of the output signal of the light-receiving element $j$ -continued b: width of a light-receiving element
f: distance o the linear array of the light-receiving elements from the surface element examined
$x_j$: distance of the light-receiving element j from the element "O", and
element "O": light-receiving element onto which the beam strikes at an "ideal" reflection on the reference element.

The profile curve of the body to be examined can be determined by integration in a simple manner from the inclination angle of the individual surface elements obtained in this way. With the device in accordance with this invention, there is also the option of choosing between inclination and vertical profile dependent, for example, on the relationship wave amplitude/wavelength or on functional demands.

A particular advantage of the device according to the invention is its uniform frequency response, i.e. its largely constant transfer function over a large frequency range. This uniform frequency response permits the output signal of the evaluation unit and/or the output signal of the integration circuit to be subjected to a Fourier transformation over a large frequency range. Statements can be deduced in a simple manner from the Fourier spectrum obtained in this way which permit a fast overview of the quality of a workpiece: For example maxima at certain Fourier orders are characteristic for chatter marks. Depending on the presence or absence of these orders, it can easily be decided whether the shaft is usable or not. By means of the Fourier analysis the angle amplitudes of the individual orders, the maximum values, can, for example, be determined and converted to the corresponding amplitudes of the vertical profile. In this way, independence from possible irritant areas, such as scratches etc., is achieved.

A particularly advantageous design of the optical part of the device in accordance with this invention is to be noted. Thanks to the "oblique incidence" of the probing light beam, a beam splitter can be dispensed with so that the intensity is not reduced. However, above all the distance relation claimed, according to which both the surface to be examined and the light-receiving device are at a distance from the lens system (measured from the relevant principal plane of the lens system) which is roughly equal to the focal length of the lens system, provides that the beams originating from the surface to be examined which originate from the illuminated surface element at a certain angle, impinge on a light-receiving element.

Independent of this, the optical axis can be rotated out of the surface normal to modify the field of view of the device.

The refinement of the device suppresses the influence of roughness in the surface perpendicular to the probe direction; in this way, the obtainable angular resolution is further increased.

By means of the dimension of the light spot in the probe direction, the smallest wavelength of form deviations still assessed can be determined. It is of advantage if the size of the light spot in the probe direction is chosen to be just large enough for the smallest wavelength which is still interesting for the measuring problem in question to be resolved.

The device in accordance with the invention does not only permit the determining of form deviations of a lower order, it is also possible to determine the roughness of the surface from the output signals of the single light-receiving elements. In this respect reference is made for details to DE-OS No. 30 37 622.

The use of photodiodes as light-receiving elements has the advantage that diode arrays with less width than the single light-receiving elements and with high sensitivity are available in standard form at reasonable prices.

The rotation of the axis of the light-receiving element array contrary to the probe direction "shortens in the projection" the width of each of the individual light-receiving elements in the direction of the form deviations so that the angular sensitivity increases.

The use of a telescope optic permits the resolution of the device according to the invention to be increased by "spreading out" the reflected light distribution on the light-receiving array.

Figure 2A:
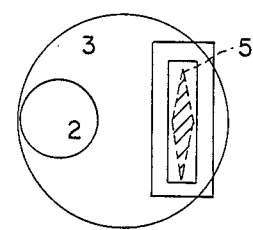
Figure 2:
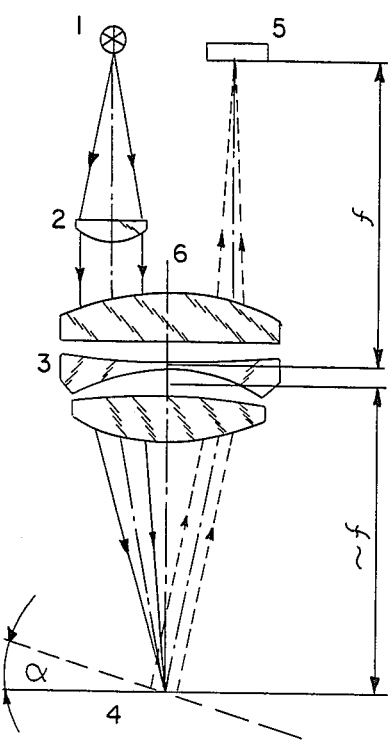
Figure 3B:
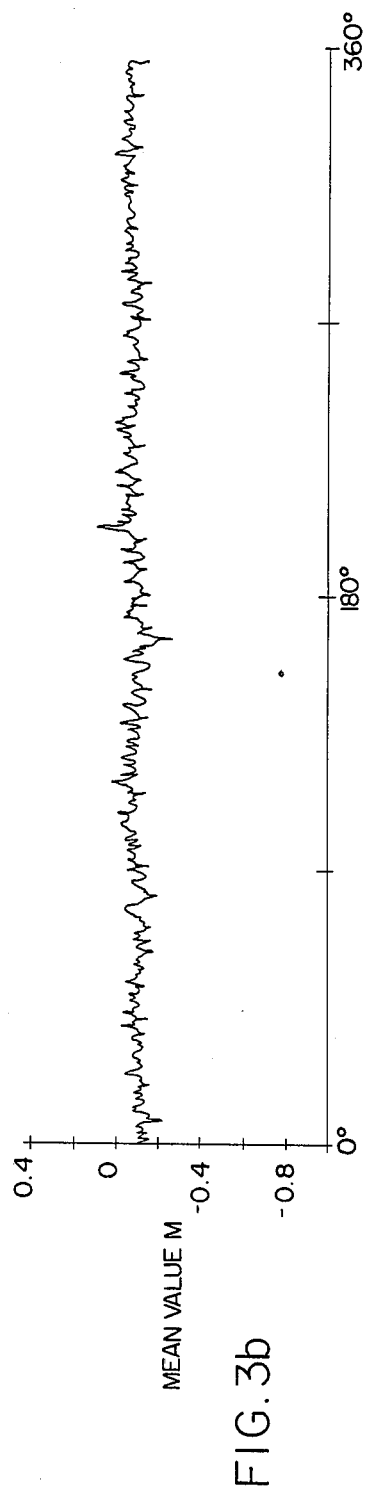
Figure 3A:
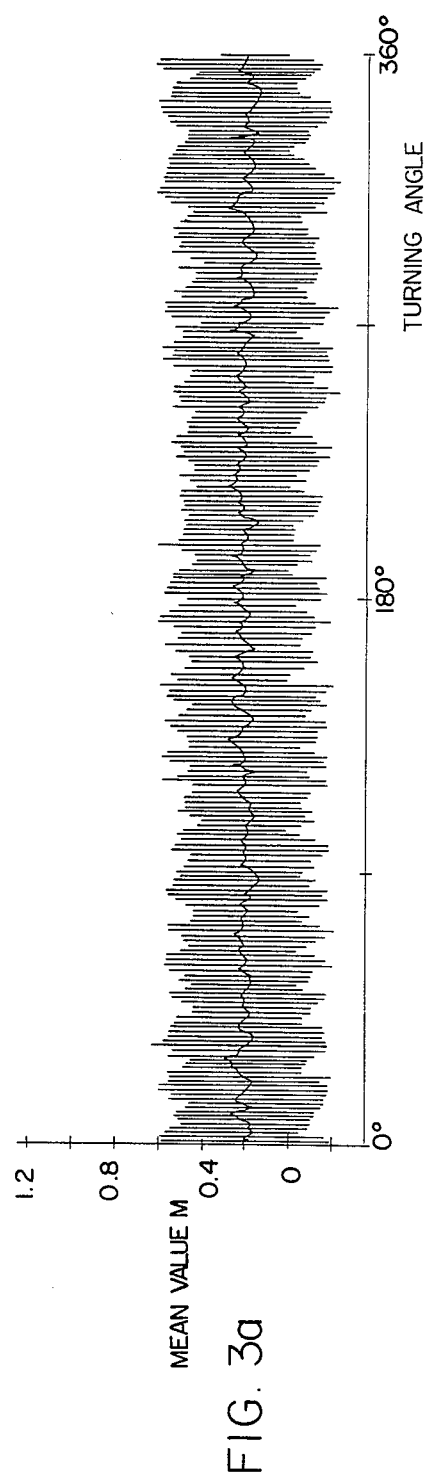
Figure 4B:
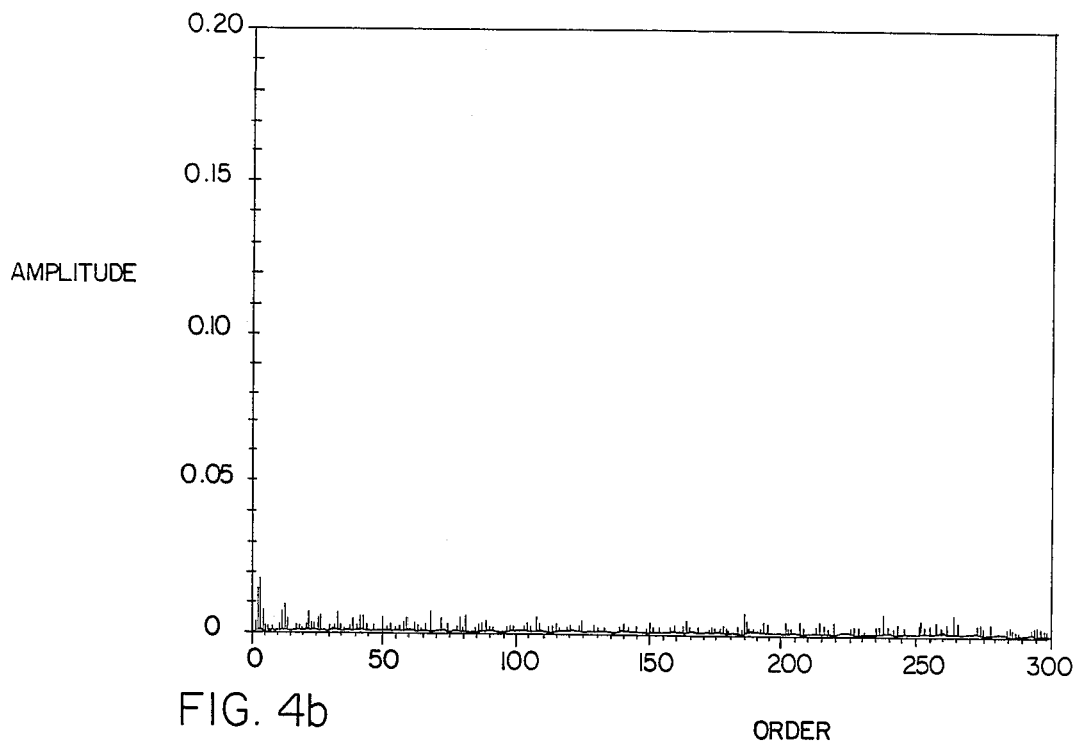
Figure 4A:
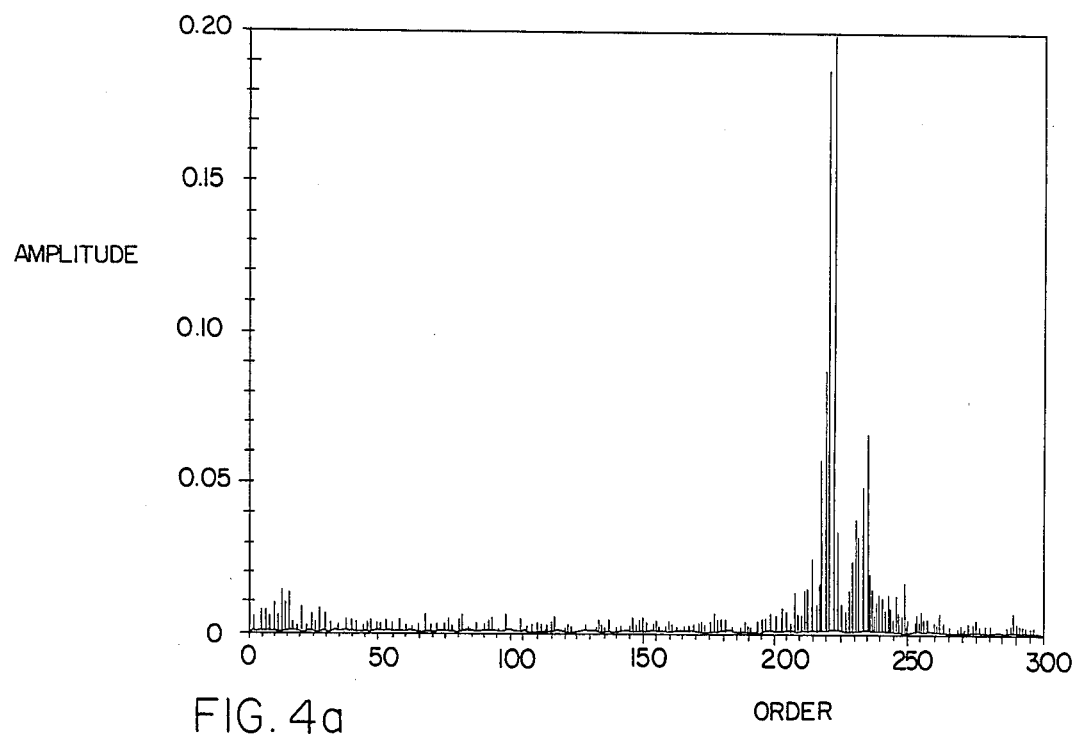
Figure 5B:
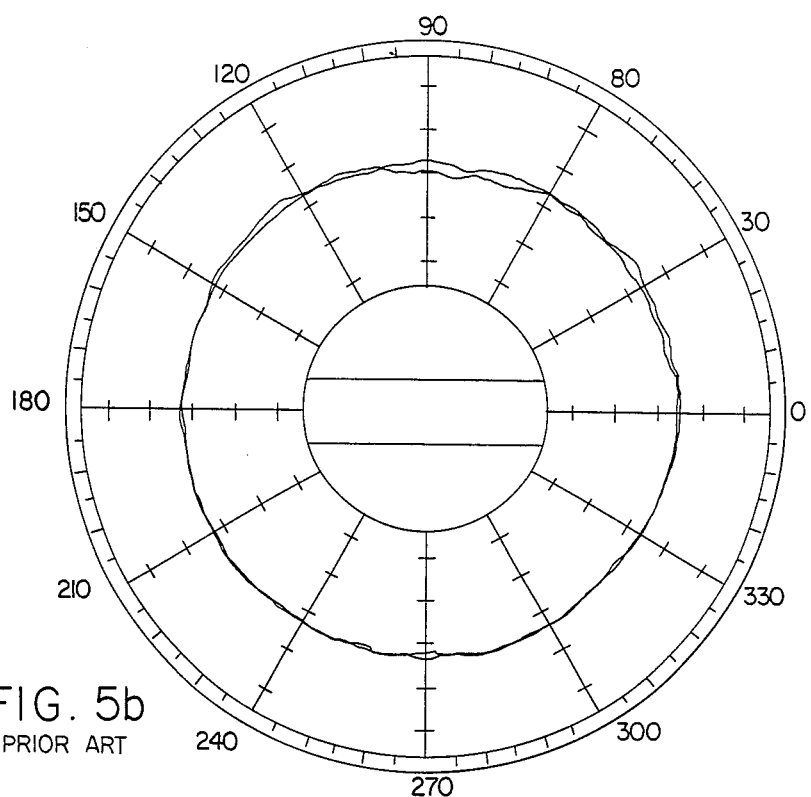
Figure 5A:
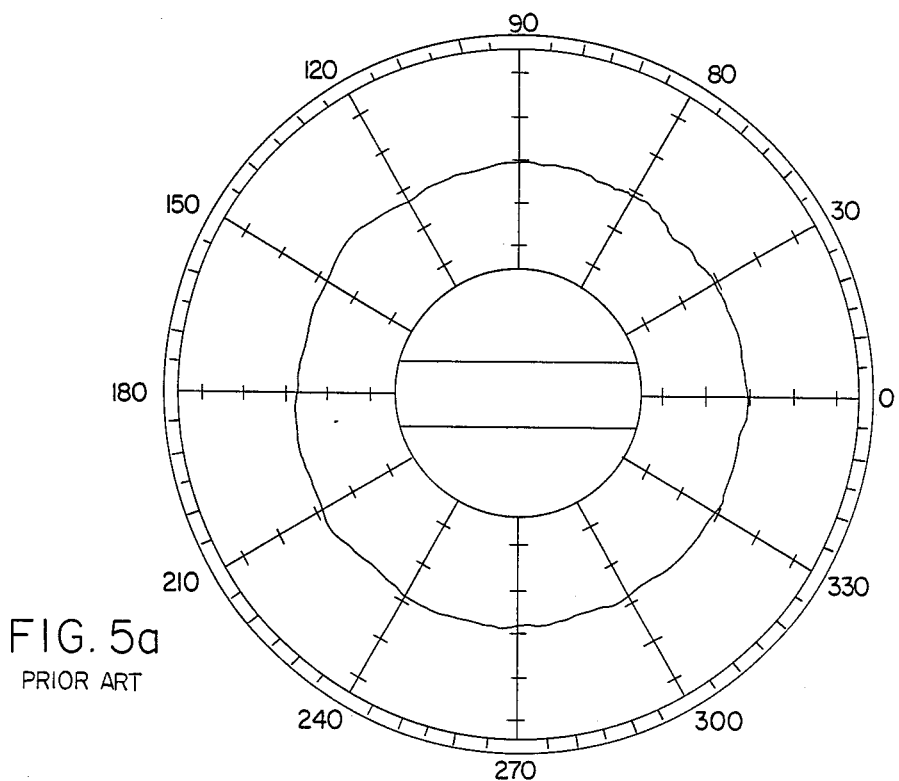

The invention is described below in detail using a version example and with reference to the drawing in which:

FIG. 1 shows an explanation of the measuring principle according to the invention, FIG. 2 shows the principle structure of a device in accordance with the invention, FIGS. 3a and b the curves of the core of the scattering distribution for a "whistling" stator shaft and for a stator shaft which causes no noise, FIGS. 4a and b Fourier transformations of the results shown in FIG. 3, and FIGS. 5a and b show for comparison purposes the results of a mechanical form testing on these stator shafts.

FIG. 1 shows an explanation of the measuring principle. The beam of a light source 1 is projected from a lens 3 on to the surface 4 to be examined. The reflected light strikes a diode array 5. Depending on the inclination of the "wavey surface" the core of the reflected light pencil will be at a different position (M1 or M2) on the diode array 5. Due to the roughness of the surface 4, the reflected light pencil shows a distribution shown in schematic form in FIG. 1. Using this distribution, which is different from surface element to surface element, the measurement of the location of the reflected light pencil with light scales is, for example, subject to a large, incorrectible error.

It should also be noted that the lens in FIG. 1 is a cylinder lens so that an elongated measuring spot 7 is produced.

FIG. 2 shows a section and a top view through a version example of a device according to the invention for the optical detection of surface errors of a low order. The device, which is shown only in schematic form, again possesses a light source 1, a collimator 2, a measuring lens 3 and a diode array 5.

The surface to be examined 4 has a distance from the device, i.e. from the front principle plane of the measuring lens 3, which is approximately equal to the focal length f of the measuring lens. The light originating from the light source 1, for example from a laser or a light-emitting diode, is (where necessary) parallelised by the collimator 2 and strikes the measuring lens 3 outside its optical axis 6. The parallel light beam is focused on the surface to be examined 4 by the measuring lens 3. The light beams originating from the individual illuminated points of the measuring spot are then projected onto the diode array by the measuring lens 3. The distance of the diode array 5 from the rear principle plane of the measuring lens 3 is, in this process, approximately equal to the focal length of the measuring lens.

Because of this spatial allocation of the surface to be examined to the measuring lens or of the measuring lens to the diode array, the light beams which originate at a certain angle from the individual points of the measuring spot on the surface 4 are projected onto one and the same diode of the diode array 5. This is implied schematically in FIG. 2. In other words, the measuring lens 3 and the test surface or the diode array 5 form a Fourier system.

In practice, it has been found that distance changes of up to 30% have no appreciable effect on the detection of surface errors of a low order.

To determine the inclination angle of the surface element probed (shown as a broken line in FIG. 2), the scattered light distribution shown schematically as a top view onto the device according to the invention on the diode array 5 is determined against a reference element (continuous line in FIG. 2) in accordance with the equation:

$$\alpha \cong \tfrac{1}{2}\tan(2\alpha) = \frac{b \cdot M}{2f} = \frac{b}{2f n_{ges}} \sum_{j=-(k-1)}^{l} n_j x_j$$

Where M =

$$\sum_{j=-(k-1)}^{l} n_j x_j / n_{ges}$$

is the M value used below which is proportional to the core position of the light spot on the diode array.
And where in the equations:

$$n_{ges} = \sum_{j=-(k-1)}^{2} n_j$$

$k + 1$: number of light-receiving elements
$n_j$: amplitude of the output signal of the light-receiving element $j$
$b$: width of a light-receiving element
$f$: distance of the linear array of the light-receiving elements from the surface element examined
$x_j$: distance of the light-receiving element $j$ from the element "0", and
element "0": light-receiving element onto which the beam strikes at an "ideal" reflection on the reference element.

In evaluating the output signals of the individual diodes of the diode array 5 in accordance with the equation shown above, a shift in the core of scattered light distribution of 1/10 of the width b of a diode can always be resolved. The resolution limit in practical use is approximately 1/100 of a diode width b.

For example, with a diode width of b=0.9 mm and a focal length f of the measuring lens 3 of 25 mm it is possible to resolve an angle of 6.2′, while with a focal length of approximately 50 mm an angle of 3.0′ can be resolved. The inclination of the beam of the measuring lens against the optical axis 6 is between 10 and 20 degrees in this process.

FIG. 3a shows the curve of the M value, i.e. of the position of the core of the reflected light pencil as a function of the rotation angle of a stator shaft which causes whistling in an installed state, while FIG. 3b shows the dependence of the M value for a stator shaft which does not cause any whistling. As can be seen, a substantially modified optical M signal curve is present for the stator shaft which causes whistling: the amplitudes are several times greater and the structure more regular. If one calculates the standard deviation of the M value as a simple characteristic for its scattering behaviour, then one obtains values of <0.1 as typical standard deviations for unflawed shafts, while the standard deviations for "whistling" shafts are larger than 0.1 and typically greater than 0.15.

FIG. 5a and 5b show the results obtained with a Perthen-Formtester of Messrs. Mahr for these shafts. Surprisingly, the roundness deviation for the flawless shaft, i.e. the shaft which does not cause any whistling when in an installed state, is at approximately 4 μm greater than the roundness deviation of the shaft causing whistling, whose roundness deviation is about 2 μm.

It can be seen from FIGS. 3 and 5 that no significant difference is shown in the protocol of the mechanical form-testing instrument, whereas the M value which has been determined in accordance with the invention does show such significant difference.

In the Fourier-transformed values of the measuring results shown in FIGS. 4a and 4b, a clear difference between shafts which cause whistling and those which do not can be seen. In the course of a systematic examination it was found that certain form errors always result in maxima in certain orders: For example, all shafts which caused whistling had maxima in about the 220th order.

In the above, the invention has been described by means of examples. Within the central idea according to the invention the most varied modifications are possible:

For example, the axis of the light-receiving array and the feed device can enclose an angle: In this way, the effective width of a light-receiving element is reduced, and so the resolution increased.

In addition, the most varied optical arrays can be used; of course, it is also possible to let the probe light beam strike the surface to be examined at almost 90°. And instead of spherical projection elements, elements with a cylinder power can also be used so that the gap geometry in the probe direction or perpendicular to same can be adapted to the measuring problem.

In every case, the device according to the invention has the advantage that with it it is also possible to measure over grooves, boreholes etc. In addition, special surface forms can be masked out by means of the software.

We claim:

1. Device for the optical detection of form errors of a low order comprising a light source for probing the body to be examined, a light-receiving device for the light reflected from the body, and an evaluation unit which determines the inclination angle ($\alpha$) of the probed surface element of the body from the output signal designated by $n_j$ of the light-receiving device, characterized by the fact that the light-receiving device consists of a number of light-receiving elements in a linear array, said angle being determined against a reference element in the surface of the body in accordance with the equation $$\alpha \cong \tfrac{1}{2}\tan(2\alpha) = \frac{b}{2n_{ges}f} \sum_{j=-(k-1)}^{l} n_j x_j$$

where $$n_{ges} = \sum_{j=-(k-1)}^{l} n_j$$

-continued

| | |
|---|---|
| $k + 1$: | number of light-receiving elements |
| $n_j$: | amplitude of the output signal of the light-receiving element $j$ |
| $b$: | width of a light-receiving element |
| $f$: | distance o the linear array of the light-receiving elements from the surface element examined |
| $x_j$: | distance of the light-receiving element $j$ from the element "$O$", and |
| element "$O$": | light-receiving element onto which the beam strikes at an "ideal" reflection on the reference element | whereby the evaluation unit determines the inclination angle from all output signals of the light-receiving elements.

2. Device according to claim 1 characterized by the fact that an integration circuit is connectable to the evaluation unit which integrates the output signal of the evaluation circuit proportional to the inclination angle of each surface element in order to determine the profile curve f(x) of the body.

3. Device according to claim 2 characterized by the fact that a transformation circuit is provided which subjects the output signal of the evaluation unit and/or the output signal of the integration circuit to a Fourier transformation.

4. Device according to claim 3 characterized by the fact that the axis of the light beam probing the surface encloses an angle other than zero with the surface normal of the ideal surface, and a lens system being provided for the projection of the reflected light onto the light-receiving device the distance of said lens system from the surface and from the light-receiving device being, in each case, approximately equal to the focal length of the lens system.

5. Device according to claim 4, characterized by the fact that the light spot probing the surface provides greater dimensions perpendicular to the probing direction than in the probing direction for an optical filtering of roughness influences.

6. Device according to claim 5, characterized by the dimension of the light spot in the probing direction being approximately equal to the wavelength of the finest form resolveable error.

7. Device according to, claim 4 characterized by the output signals of the light-receiving elements being adapted for determination of the roughness of the surface examined.

8. Device according to claim 7 wherein the evaluation unit determining the roughness of the surface from the output signals of the light-receiving elements according to the equation $$S_x = \sum_{i=1}^{k+l} |w_i - w|^x P_i;\ x = 1 \text{ or } 2$$

$$w = \sum_{i=1}^{k+l} w_i P_i$$

$$P_i = w_i g_i / \left( \sum_{i=1}^{k+l} w_i g_i \right)$$

where,
$w_i$: the angle of scattered light obtained from each light-receiving element,
$k + l$ the number of light-receiving elements
$w$ the mean value from the values $P_i$ and $w_i$,
$P_i$ the measuring signal $n_i$ normed according to equation (c), and
$g_i$ correction factors for the measuring signal $n_i$.

9. Device according to claim 8, wherein the light-receiving element is a diode array.

10. Device according to claim 9, wherein the axis of the light-receiving element array encloses an acute angle with the probing direction.

11. Device according to claim 10 wherein a telescopic optic projects reflected light onto the light-receiving device.

* * * * *